(12) United States Patent
Shecterle et al.

(10) Patent No.: US 7,981,376 B2
(45) Date of Patent: Jul. 19, 2011

(54) PROCESSES FOR THE ISOMERIZATION OF NORMAL BUTANE TO ISOBUTANE

(75) Inventors: David J. Shecterle, Arlington Heights, IL (US); Dale J. Shields, Grayslake, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/629,067

(22) Filed: Dec. 2, 2009

(65) Prior Publication Data

US 2010/0080739 A1    Apr. 1, 2010

Related U.S. Application Data

(62) Division of application No. 11/851,575, filed on Sep. 7, 2007, now Pat. No. 7,638,675.

(51) Int. Cl.
| | |
|---|---|
| *B01J 8/02* | (2006.01) |
| *B01J 35/02* | (2006.01) |
| *B01J 8/00* | (2006.01) |
| *B01J 10/00* | (2006.01) |
| *B01J 19/00* | (2006.01) |
| *C07C 5/13* | (2006.01) |
| *C07C 7/144* | (2006.01) |

(52) U.S. Cl. ........ 422/211; 422/129; 422/187; 422/234; 585/738; 585/818

(58) Field of Classification Search .................. 422/187, 422/234, 129, 211; 585/738, 818

See application file for complete search history.

(56) References Cited

U.S. PATENT DOCUMENTS

| | | | |
|---|---|---|---|
| 6,338,791 B1 * | 1/2002 | Ragil et al. ................ | 208/63 |
| 2006/0201884 A1 * | 9/2006 | Kulprathipanja et al. .... | 210/651 |
| 2008/0312483 A1 * | 12/2008 | Ichikawa et al. .............. | 585/430 |
| 2009/0247805 A1 * | 10/2009 | Bournay et al. ............... | 585/738 |
| 2010/0080739 A1 * | 4/2010 | Shecterle et al. ............. | 422/187 |

FOREIGN PATENT DOCUMENTS

| | | | |
|---|---|---|---|
| WO | WO 2005/049766 A1 * | 6/2005 | |
| WO | WO 2006/011568 A1 * | 2/2006 | |
| WO | WO 2006/099254 A1 * | 9/2006 | |
| WO | WO 2006/099287 A1 * | 9/2006 | |

OTHER PUBLICATIONS van de Graaf et al, Effect of Operating Conditions and Membrane Quality on the Separation Performance of Composite Silicalite-1 Membranes, 1998, Ind. Eng. Chem. Res., 37, 4071-4083.*

* cited by examiner

*Primary Examiner* — Walter D Griffin
*Assistant Examiner* — Natasha Young
(74) *Attorney, Agent, or Firm* — Maryann Maas

(57) ABSTRACT

In a normal butane isomerization process where the isomerization effluent (108, 114) is fractionated in a deisobutanizer (116) operated such that a lower boiling fraction (118) is provided containing at least 80 mass-% isobutane and a higher boiling fraction (122) containing normal butane and at least 10 mass-% isobutane. The higher boiling fraction (122) is contacted with a selectively permeable membrane (124) to provide a permeate (126) containing normal butane-containing and a retentate (128) containing at least 80 mass-% isobutane. The preferred membranes are sieving membranes having a $C_4$ Permeate Flow Index of at least 0.01 and a $C_4$ Permeate Flow Ratio of at least 1.25:1.

5 Claims, 2 Drawing Sheets

PROCESSES FOR THE ISOMERIZATION OF NORMAL BUTANE TO ISOBUTANE

CROSS-REFERENCE TO RELATED APPLICATION

This application is a Division of application Ser. No. 11/851,575 filed Sep. 7, 2007, now U.S. Pat. No. 7,638,675, the contents of which are hereby incorporated by reference in its entirety.

BACKGROUND OF THE INVENTION

This invention relates to improved processes for the isomerization of normal butane to isobutane using a deisobutanizer in combination with a membrane that is selectively permeable to normal butane as compared to isobutane and to improved processes using a membrane to recover at least a portion of isobutane contained in the normal butane-containing feedstock for the isomerization. Processes for the isomerization of normal butane to isobutane are widely practiced. The isomerization process proceeds toward a thermodynamic equilibrium. Hence, the isomerate will still contain a substantial concentration of normal butane, usually in the range of a mole ratio of isobutane to normal butane of 1.2:1 to 2:1. The sought isobutane product, usually having a purity of at least 80, often at least 90 or more, e.g., 95 to 99, mol-% isobutane, is obtained by distillation (deisobutanizer) to obtain the relatively pure isobutane product as an overhead and a normal butane-containing fraction which is recycled to the isomerization reactor.

As the boiling points of normal butane and isobutane are relatively close and a relatively pure isobutane product is desired, the deisobutanizer typically is operated with a high reflux ratio. Thus, the heat duty of the deisobutanizer is a significant component of the operating costs of a butane isomerization process, and the heat duty becomes increasingly significant as higher purity isobutane product streams are sought. Accordingly, improved normal butane isomerization processes are sought that have improved capital and operating costs.

Separation of linear from branched paraffins, e.g., normal butane and isobutane, has been proposed, but membranes have yet to find a practical, commercial application. U.S. Pat. No. 5,069,794 discloses microporous membranes containing crystalline molecular sieve material. At column 8, lines 11 et seq., potential applications of the membranes are disclosed including the separation of linear and branched paraffins. See also, U.S. Pat. No. 6,090,289, disclosing a layered composite containing molecular sieve that could be used as a membrane. Among the potential separations in which the membrane may be used that are disclosed commencing at column 13, line 6, of the patent include the separation of normal paraffins from branched paraffins. U.S. Pat. No. 6,156,950 and U.S. Pat. No. 6,338,791 discuss permeation separation techniques that may have application for the separation of normal paraffins from branched paraffins and describe certain separation schemes in connection with isomerization. US 2003/0196931 A1 discloses a two-stage isomerization process for up-grading hydrocarbon feeds of 4 to 12 carbon atoms. The use of zeolite membranes is suggested as a suitable technique for separating linear molecules. See, for instance, paragraphs 0008 and 0032. U.S. Pat. No. 6,818,333 discloses thin zeolite membranes that are said to have a permeability of n-butane of at least $6 \cdot 10^{-7}$ mol/m$^2$·s·Pa and a selectivity of at least 250 of n-butane to isobutane.

Due to the volumes of normal butane-containing feeds that are processed in commercial-scale butane isomerization units, large membrane surface areas would have to be provided in order to achieve the sought separation of the linear paraffins. For instance, ZSM-5/Silicalite (MFI) membranes (a sieving membrane) available from NGK Insulators, Ltd., Japan, that have selectivity for the permeation of linear paraffins over branched paraffins, have a flux under operating conditions in the range of 0.1 to 1.0 milligram moles per second per square meter at a pressure differential of 15 to 500 kPa. Thus, the costs for commercially implementing such a membrane separation system using these membranes or the membranes of the type disclosed in U.S. Pat. No. 6,818,333 render it not competitive with respect to an adsorption separation system or a distillation separation such as a deisobutanizer.

Recently, Bourney, et al., in WO 2005/049766 disclose a process for producing high octane gasoline using a membrane to remove, inter alia, n-pentane from an isomerized stream derived from the overhead of a deisohexanizer. A side cut from the deisohexanizer is as a sweep fluid on the permeate side of the membrane. The mixture of the permeate and sweep fluid is recycled to the isomerization reactor. In a computer simulation based upon the use of an MFI on alumina membrane, example 1 of the publication indicates that 5000 square meters of membrane surface area is required to remove 95 mass percent of n-pentane from the overhead from a deisohexanizer distillation column. At the flow rate of feed to the permeator (75000 kg/hr. having 20.6 mass percent n-pentane), the flux of n-pentane used in the simulation appears to be in the order of 0.01 gram moles/m$^2$·s at 300° C.

For the purposes of the following discussion of the invention, the following membrane properties are defined.

Microporous

Microporous and microporosity refer to pores having effective diameters of between 0.3 to 2 nanometers.

Mesoporous

Mesoporous and mesoporosity refer to pores having effective diameters of between 2 and 50 nanometers.

Macroporous

Macroporous and macroporosity refer to pores having effective diameters of greater than 50 nanometers.

Nanoparticle

Nanoparticles are particles having a major dimension up to 100 nanometers.

Molecular Sieves

Molecular sieves are materials having microporosity and may be amorphous, partially amorphous or crystalline and may be zeolitic, polymeric, metal, ceramic or carbon.

Sieving Membrane

Sieving membrane is a composite membrane containing a continuous or discontinuous selective separation medium containing molecular sieve barrier. A barrier is the structure that exists to selectively block fluid flow in the membrane. In a continuous sieving membrane, the molecular sieve itself forms a continuous layer that is sought to be defect-free. The continuous barrier may contain other materials such as would be the case with mixed matrix membranes. A discontinuous sieving membrane is a discontinuous assembly of molecular sieve barrier in which spaces, or voids, exist between particles or regions of molecular sieve. These spaces or voids may contain or be filled with other solid material. The particles or regions of molecular sieve are the barrier. The separation effected by sieving membranes may be on steric properties of the components to be separated. Other factors may also affect permeation. One is the sorptivity or lack thereof by a component and the material of the molecular sieve. Another is the interaction of components to be separated in the microporous structure of the molecular sieve. For instance, for some zeolitic molecular sieves, the presence of a molecule, say, n-hexane, in a pore, may hinder 2-methylpentane from entering that pore more than another n-hexane molecule. Hence, zeolites that would not appear to offer much selectivity for the separation of normal and branched paraffins solely from the standpoint of molecular size, may in practice provide greater selectivities of separation.

$C_4$ Permeate Flow Index

The permeability of a sieve membrane, i.e., the rate that a given component passes through a given thickness of the membrane, often varies with changes in conditions such as temperature and pressure, absolute and differential. Thus, for instance, a different permeation rate may be determined where the absolute pressure on the permeate side is 1000 kPa rather than that where that pressure is 5000 kPa, all other parameters, including pressure differential, being constant. Accordingly, a $C_4$ Permeate Flow Index is used herein for describing sieve membranes. The $C_4$ Permeate Flow Index for a given membrane is determined by measuring the rate (gram moles per second) at which a substantially pure normal butane (preferably at least 95 mass-% normal butane) permeates the membrane at approximately 150° C. at a retentate side pressure of 1000 kPa absolute and a permeate-side pressure of 100 kPa absolute. The $C_4$ Permeate Flow Index reflects the permeation rate per square meter of retentate-side surface area but is not normalized to membrane thickness. Hence, the $C_4$ Permeate Flow Index for a given membrane will be in the units of gram moles of normal butane permeating per second per square meter of retentate-side membrane surface area.

$C_4$ Permeate Flow Ratio

The $C_4$ Permeate Flow Ratio for a given sieve membrane is the ratio of the $C_4$ Permeate Flow Index (n-butane) to an i-$C_4$ Permeate Flow Index wherein the i-$C_4$ Permeate Flow Index is determined in the same manner as the $C_4$ Permeate Flow Index but using substantially pure isobutane (preferably at least 95 mass-% isobutane).

SUMMARY OF THE INVENTION

By this invention, improvements are made to normal butane isomerization processes of normal butane-containing feedstocks where the processes use distillation (deisobutanizer) to recover a purified isobutane product from an isomerization effluent. The processes of this invention provide for the integration of a membrane separation with a deisobutanizer to reduce reboiler duty on the deisobutanizer and enable a deisobutanizer to be debottlenecked or to have a reduced diameter and number of distillation trays for a given production rate and purity of isobutane product.

In many instances, the distillation serves to provide a normal butane-containing fraction for recycle to isomerization reactors. In accordance with this invention, the deisobutanizer is operated with a sufficiently low reflux ratio to provide a normal butane-containing fraction that contains a significant concentration of isobutane, often at least 10, and sometimes at least 25, mass-% isobutane and a lower boiling fraction having an isobutane content of at least 80, preferably at least 90, and sometimes between 95 and 99, mass-%.

Thus the heat duty, and hence operating costs, for the distillation can be substantially reduced for a given isobutane product production rate and purity. For instance, the reflux to feed mass ratio may in some instances be reduced by at least 20 percent. Typically, reflux to feed ratios for such distillation columns are in the order of 2.5 to 4:1. By using the processes of this invention, the reflux to feed ratios may be reduced to 0.5:1 to 3:1, preferably 0.5:1 to 3:1, say, 0.5 to 2:1, and more preferably to 0.75:1 to 1.3:1 for the same isobutane production rate and purity.

In the processes of this invention, the normal butane-containing fraction from the distillation is contacted with the retentate side of a selectively permeable membrane to provide a permeate enriched in normal butane and a retentate containing at least 80 mass-% isobutane. Since the volume of the normal butane-containing fraction is only a portion of the effluent from the isomerization reactor, the surface area of membrane required is less than that required where a membrane separation is used to separate isobutane from the isomerization reactor effluent. Moreover, while isobutane is present in the feed to the membrane, it is in a minor concentration in a stream that is a fraction of the isomerization reactor effluent. Hence, permeation of some isobutane through the membrane can be tolerated since the absolute amount of isobutane in the recycle to the isomerization reactor will have little effect on achieving a high per-pass conversion of normal butane in the fresh feedstock. Consequently, suitable membranes include not only those with high selectivities for the separation of normal butane from isobutane, but also those that exhibit a high $C_4$ Permeate Flow Index even if accompanied by a low $C_4$ Permeate Flow Ratio.

In one broad aspect of the processes of this invention relating to the use of distillation to provide a purified isobutane-containing product comprise:

(a) isomerizing an isomerization feed comprising at least 50 mass-% normal butane under isomerization conditions including the presence of isomerization catalyst to provide an isomerization effluent containing isobutane and containing normal butane but in a concentration less than that in the isomerization feed;

(b) distilling at least a portion, preferably at least 90 mass-% and most preferably essentially all, of the isomerization effluent to provide (i) a lower boiling fraction containing isobutane and lighter paraffins wherein at least 80, preferably at least 90, mass-% of the lower boiling fraction is isobutane and (ii) a higher boiling, normal butane-containing fraction containing normal butane and at least 10 mass-% isobutane;

(c) contacting at least a portion, preferably at least 90 mass-% and most preferably essentially all, of the normal butane-containing fraction from step (b) with a retentate-side of a selectively permeable membrane under conditions including sufficient membrane surface area and pressure differential across the membrane to provide a retentate fraction containing at least 80, preferably at least 90, mass-% isobutane, and to provide across the membrane at a permeate-side, a permeate fraction having an increased concentration of normal butane, said permeate fraction preferably containing at least 90 mass-% of the normal butane contained in the normal butane-containing fraction contacted with the membrane; and (d) withdrawing from step (c) the retentate fraction, preferably for combination with the lower boiling fraction from step (b).

The isomerization feed may be a normal butane-containing feedstock or it may be a stream derived from a normal butane-containing feedstock from which at least a portion of any isobutane contained therein has been removed, e.g., by distillation or membrane separation, including membrane separation by another broad aspect of this invention. Thus the normal butane-containing feedstocks may contain as little as 30 mass-% normal butane but yet be suitable for use in the processes of this invention. In preferred embodiments of the processes of this invention, at least a portion, preferably at least 90 mass-% and most preferably essentially all, of the permeate fraction of step (c) is passed to step (a).

Preferably the lower boiling fraction of step (b) contains at least 25, preferably 30 to 95, and in some instances from 30 to 80, mass-% of the isobutane in the isomerization effluent. In general, for a given reflux to feed ratio, increasing the purity of the isobutane in the product will decrease the isobutane concentration in the lower boiling fraction.

In preferred embodiments of this invention, at least 50 mass-% of the isobutane contained in the normal butane-containing fraction contacted with the membrane is retained in the retentate fraction. The concentration of the normal butane in the permeate fraction is often at least 50, preferably at least 70, mass-%.

Another broad aspect of the processes of this invention pertain to subjecting at least a portion of the normal butane-containing feedstock to a membrane separation to remove isobutane and thus provide a higher concentration of normal butane in the feed to the isomerization reactor. Often normal butane-containing feeds contain significant amounts of isobutane, e.g., from 5 or 10 mass-% to upwards of 50 or 60 mass-%. As the isomerization is equilibrium driven, the presence of isobutane in the isomerization feed deleteriously affects the conversion of normal butane to isobutane as well as increases the flow rate of feedstock through the isomerization reaction zone. Hence, typically such isobutane containing feedstocks are distilled to remove a least a portion of the isobutane. For instance, the feedstock to an isomerization unit may be introduced into the deisobutanizer. While a deisobutanizer does recover isobutane from the feedstock and thus increase the concentration of normal butane in the fluid fed to the isomerization reaction zone, not only must the deisobutanizer be sized to handle the additional volume of fluid, but also, the heat duty of the deisobutanizer is increased.

In accordance with an aspect of this invention, membrane separation is used to remove isobutane from the feedstock. In the broadest terms of this aspect of the invention, distillation of the isomerization effluent is not essential. The broad aspects of the normal butane isomerization processes of this aspect of the invention comprise: (a) contacting at least a portion, preferably at least 90 mass-% and most preferably essentially all, of a normal butane-containing feedstock also containing at least 5, often at least 10, mass-% isobutane with a retentate-side of a selectively permeable membrane under conditions including sufficient membrane surface area and pressure differential across the membrane to provide a retentate fraction containing at least 80, preferably at least 90, mass-% isobutane, and to provide across the membrane at a permeate-side, a permeate fraction having an increased concentration of normal butane, said permeate fraction preferably containing at least 80 mass-% of the normal butane contained in the feedstock contacted with the membrane; and (b) subjecting the permeate fraction to isomerization conditions including the presence of isomerization catalyst to provide an isomerization effluent containing normal butane but in a concentration less than that in the feedstock.

In one embodiment, the retentate from step (a) is combined with the isomerization effluent and thus can provide an isobutane product of adequate purity even without distillation to remove normal butane. Alternatively, the retentate can be used as a product stream itself or combined with the lower boiling fraction from a distillation.

Preferably, the isomerization effluent is refined to provide a product stream containing at least 80, preferably at least 90, mass-% isobutane and a normal butane-containing stream, at least a portion of which may or may not be recycled for isomerization. Often at least 50, preferably at least 60 to essentially 100, mass-% of the isobutane contained in the feedstock is contained in the retentate fraction.

Preferably in both broad aspects of the invention, the membrane is a sieving membrane having a $C_4$ Permeate Flow Index of at least 0.01, more preferably at least 0.02, and a $C_4$ Permeate Flow Ratio of at least 1.25:1, more preferably at least 1.3:1, and often 1.35:1 to 5:1 or 6:1.

The invention also pertains to apparatus for conducting the processes of the invention. In a broad aspect, the apparatus for the isomerization of feedstock containing normal butane comprises:

a. an isomerization reactor (106) adapted to isomerize normal butane to an isobutane-containing isomerate having an inlet and an outlet for isomerate;

b. a distillation column (116) having an inlet in fluid communication with the outlet of isomerization reactor (106) a lower boiling fraction outlet conduit (118) and a higher boiling fraction outlet conduit (122), said distillation column (116) being adapted to distill at least a portion of the isobutane-containing isomerate to provide a lower boiling fraction richer in isobutane than the isomerate and a higher boiling fraction richer in normal butane than the isomerate, said fraction containing isobutane; and c. a membrane separator (124) having a feed side inlet in fluid communication with the higher boiling fraction conduit (122), a feed side outlet in fluid communication with line (118) from the lower boiling outlet of distillation column (116), and a permeate outlet in fluid communication with the inlet of the isomerization reactor (106).

DETAILED DISCLOSURE

Isomerization

Figure 1:
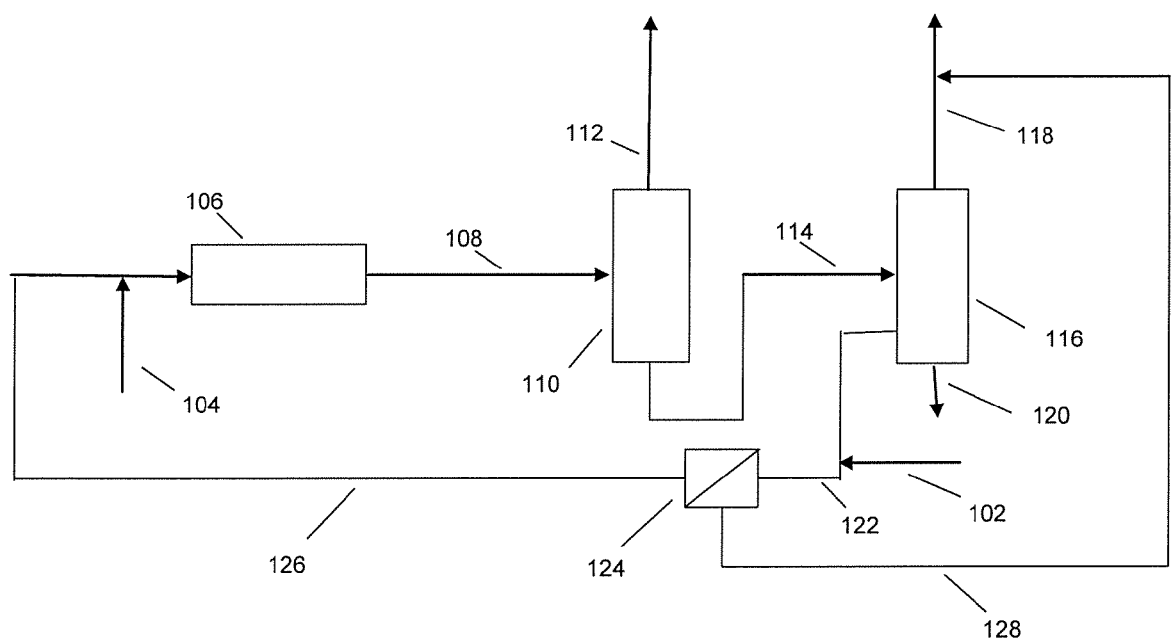
FIG. 1 is a schematic representation of processes in accordance with this invention using a stabilizer column prior to a deisobutanizer.

Any suitable normal butane-containing feedstock may be used in the processes of this invention. The feedstock may be obtained from any suitable source including, but not limited to fractionation or liquefaction of gaseous or normally liquid petroleum stocks, from synthetic paraffins such as from Fischer-Tropsch processes, cracking of higher molecular weight hydrocarbons and the like. The composition of the feedstock will depend upon the source of the feedstock. The preferred feedstocks will contain at least 30, say, 50 to essentially 100, mass-% normal butane. Other components that may be present include isobutane, butenes, and lighter and heavier hydrocarbons. Generally, lighter hydrocarbons are present in less than 20, preferably less than 5, mass-% and heavier hydrocarbons are present in amounts less than 10, preferably less than 5, mass-%. In the event that the feedstock contains $C_5$ or heavier hydrocarbons, it is usually preferred that the feedstock be subjected to a unit operation such as distillation (for instance in a deisobutanizer) to reduce the concentration of $C_5$ and heavier hydrocarbons to less than 1, preferably less than 0.5, mass-%.

The feedstock together with a recycle, if any, recovered from the isomerization reaction effluent is passed as the isomerization feed to one or more isomerization zones. The feedstock and recycle are usually admixed prior to entry into the isomerization zone, but if desired, may be separately introduced. Alternatively, the feedstock may be combined with the isomerization effluent in the deisobutanizer and then passed to the isomerization zones in combination with the recycle. This latter technique serves to recover from the feedstock at least a portion of the isobutane contained therein. In each case, the total feed to the isomerization zone is referred to herein as the isomerization feed. The recycle may be provided in one or more streams. As discussed later, the recycle contains normal butane.

The concentration of normal butane in the isomerization feed will not only depend upon the concentration of normal butane in the feedstock but also its concentration in the recycle, if any, and the relative amount of recycle to feedstock, which can fall within a wide range. Often, the isomerization feed has a normal butane concentration of at least 50, say, between 60 and 100, preferably 75 to 90, mass-%.

In the isomerization zone the isomerization feed is subjected to isomerization conditions including the presence of isomerization catalyst preferably in the presence of a limited amount of hydrogen. The isomerization of normal butane is generally considered a reversible first order reaction. Thus, the isomerization reaction effluent will contain a greater concentration of isobutane and a lesser concentration of normal butane than does the isomerization feed. In preferred embodiments of this invention, the isomerization conditions are sufficient to isomerize at least 20, preferably, between 30 and 60, mass-% of the normal paraffins in the combined feedstock and recycle. In general, the isomerization conditions achieve at least 70, preferably at least 75, say, 75 to essentially 100, percent of equilibrium for $C_4$ paraffins present in the isomerization feed. In many instances, the isomerization reaction effluent has a mass ratio of isobutane to normal butane of at least 1.2:1, preferably between 1.4 to 2:1.

The isomerization catalyst is not critical to the broad aspects of the processes of this invention, and any suitable isomerization catalyst may find application. Suitable isomerization catalysts include acidic catalysts using chloride for maintaining the sought acidity. The isomerization catalyst may be amorphous, e.g. based upon amorphous alumina, or zeolitic. A zeolitic catalyst would still normally contain an amorphous binder. The catalyst may comprise a platinum group metal on chlorided alumina.

Contacting within the isomerization zones may be effected using the catalyst in a fixed-bed system, a moving-bed system, a fluidized-bed system, or in a batch-type operation. A fixed-bed system is preferred. The reactants may be contacted with the bed of catalyst particles in upward, downward, or radial-flow fashion. The reactants may be in the liquid phase, a mixed liquid-vapor phase, or a vapor phase when contacted with the catalyst particles, with excellent results being obtained by application of the present invention to a primarily vapor-phase operation. The isomerization zone may be in a single reactor or in two or more separate reactors with suitable means to ensure that the desired isomerization temperature is maintained at the entrance to each zone. Two or more reactors in sequence are preferred to enable improved isomerization through control of individual reactor temperatures and for partial catalyst replacement without a process shutdown.

Isomerization conditions in the isomerization zone include reactor temperatures usually ranging from 40° to 250° C. Lower reaction temperatures are generally preferred in order to favor equilibrium mixtures having the highest concentration of isobutane and to minimize cracking of the feed to lighter hydrocarbons. Temperatures in the range of from 100° to 200° C. are preferred in the present invention. Reactor operating pressures generally range from 100 kPa to 10 MPa absolute, preferably between 0.5 and 4 MPa absolute. Liquid hourly space velocities range from 0.2 to 25 volumes of isomerizable hydrocarbon feed per hour per volume of catalyst, with a range of 0.5 to 15 $hr^{-1}$ being preferred.

Hydrogen is admixed with or remains with the combined feedstock and recycles to the isomerization zone to provide a mole ratio of hydrogen to hydrocarbon feed of from 0.01 to 20. The hydrogen may be supplied totally from outside the process or supplemented by hydrogen recycled to the feed after separation from isomerization reactor effluent. Light hydrocarbons and small amounts of inerts such as nitrogen and argon may be present in the hydrogen. Water should be removed from hydrogen supplied from outside the process, preferably by an adsorption system as is known in the art. In a preferred embodiment the hydrogen to hydrocarbon mol ratio in the reactor effluent is equal to or less than 0.05, generally obviating the need to recycle hydrogen from the reactor effluent to the feed.

Especially where a chlorided catalyst is used for isomerization, the isomerization reaction effluent is contacted with a sorbent to remove any chloride components or is distilled or stripped to remove the chloride components as well as light ends.

Feedstock Treatment

In the aspects of this invention in which the feedstock is subjected to membrane separation, the preferred feedstocks contain at least 5 mass-% isobutane. At least a portion, preferably at least 80, and more preferably at least 90, mass-% of the feedstock is subjected to the membrane separation prior to being introduced into the isomerization reaction zone. The feedstock may be subjected to the membrane separation immediately prior to being supplied to the isomerization unit or may be supplied to the isomerization unit upstream of a membrane separator used to recover isobutane from a normal butane containing stream. For instance, the feedstock may be fed to a deisobutanizer or between a deisobutanizer and a membrane separator used to recover isobutane from a normal butane-containing fraction being recycled to the isomerization reaction zone.

Feedstock is contacted with the retentate side of a selective membrane to provide a retentate fraction of the isomerization reaction effluent that contains at least 80 mass-% isobutane, and to provide across the membrane at a permeate-side, a permeate fraction having an increased concentration of normal butane. A pressure drop is maintained across the membrane in order to effect the desired separation at suitable permeation rates. The membrane may be of any suitable type including diffusion and sieving, and may be constructed of inorganic, organic or composite materials. For diffusion membranes, the driving force is the differential in partial pressures between the retentate and the permeate sides. In sieving membranes, the absolute pressure drop becomes a significant component of the driving force independent of partial pressures or concentrations. The preferred membranes are sieving membranes having a $C_4$ Permeate Flow Index of at least 0.01 and a $C_4$ Permeate Flow Ratio of at least 1.25:1. The sieving membranes are discussed in more detail below.

In the membrane separations, the pressure drop is often in the range of 0.1 to 10, preferably 0.2 to 2, MPa. In practice, the normal butane-containing fraction will be contacted with the retentate side of the membranes without additional compression to minimize capital and operating costs. The temperature for the membrane separation will depend in part on the nature of the membrane and on the temperature of the feedstock. Often the temperature is in the range of 25° C. to 150° C. The conditions of the membrane separation may provide for a liquid or vapor or mixed phase (the terms "mixed phase" as used herein means mixed liquid and vapor phase) on the retentate side of the membrane. The permeate may be vapor, liquid or mixed phase. If the fluid on the retentate side of the membrane is in the liquid phase, the permeate may be liquid, vapor or mixed phase.

Any suitable selectively permeable membrane may be used in the apparatus and processes of this invention. The preferred membranes are sieving membranes. The membranes used in the processes of this invention are characterized in having high flux, i.e., having a $C_6$ Permeate Flow Index of at least 0.01. The membranes may be in any suitable form such as hollow fibers, sheets, and the like which can be assembled in a separator unit such as bundled hollow fibers or flat plate or spiral wound sheet membranes. The physical design of the membranes should enable, when assembled in the separator unit, sufficient pressure drop across the membrane to provide desirable flux. For hollow fiber membranes, the high pressure side (retentate side) is usually at the outside of the hollow fiber. The flow of the permeate may be co-current, counter-current or cross-current with respect to the flow of the fluid on the retentate side of the membrane. Sufficient membrane surface area is provided that under steady state conditions the desired isobutane concentration in the retentate fraction is obtained.

Isomerization Effluent and Distillation

The isomerization effluent is subjected to one or more separation operations to remove components such as hydrogen, lower alkanes and, especially with respect to chlorided catalysts, halogen compounds.

In accordance with the aspects of this invention wherein a distillation is used to provide isobutane product, the isomerization effluent is passed either directly or with the above described intervening unit operations to a distillation assembly (which will be referenced as a deisobutanizer for the purpose of the following discussion) to provide a lower boiling fraction containing isobutane and a higher boiling, normal butane-containing fraction. As isomerization conditions tend to produce lighter components such as methane, ethane and propane, these components are either removed in a stabilizer column or removed as an overhead from the deisobutanizer. Where the lights have been substantially removed from the isomerization effluent prior to introduction into the deisobutanizer, the lower boiling isobutane fraction may be the overhead. The feed to the deisobutanizer may be vapor, liquid or mixed phase.

Most often, the deisobutanizer is adapted to provide the normal butane-containing stream as a side stream and provides a bottoms stream comprising $C_5$ components such as normal pentane and isopentane. The deisobutanizer may be a packed or trayed column and typically operates with a top pressure of between 100 and 1000 kPa (gauge) and a bottoms temperature of between 60° and 170° C. The reflux to feed ratio of the deisobutanizer will affect the concentration of isobutane in the normal butane-containing fraction. Generally, lower reflux ratios are preferred from the standpoint of reducing the heat duty for the deisobutanizer. Hence, reflux ratios (reflux to feed on a mole basis) of between 0.5:1 and 3:1 are preferred. As reflux ratios are reduced, the lower boiling fraction will contain for a given isobutane purity, a lesser portion of isobutane that is fed to the deisobutanizer. Similarly, for higher isobutane concentrations in the lower boiling effluent to be achieved, higher reflux ratios are required, all else remaining the same.

The lower boiling fraction from the deisobutanizer typically contains at least 80, and preferably at least 90, mass-% isobutane. For some downstream operations, higher purity fractions may be desired and the processes of this invention are capable for providing fractions of greater than 95 or 97 mass-%, and even as high as 99 mass-% with economic operations while still obtaining the benefit of a reduced heat duty for the deisobutanizer.

One or more other fractions can be provided by the deisobutanizer including a normal butane-containing fraction. This normal butane-containing fraction also contains isobutane as a consequence of lower reflux to feed ratios permitted by the use of the membrane separation in accordance with this invention. Often the normal butane-containing fraction will contain at least 10, preferably 20 to 50, mass-% isobutane with the balance being essentially normal butane. If the deisobutanizer is provided with a bottoms stream, $C_5$ hydrocarbons are removed at that point, otherwise, they will be additional components in the normal butane-containing stream.

At least a portion, preferably at least 80, and more preferably at least 90, mass-% to substantially all of the normal butane-containing fraction from the deisobutanizer is contacted with the retentate side of a selective membrane. A retentate fraction is provided that contains at least 80, and preferably at least 90, mass-% isobutane, and to provide across the membrane at a permeate-side, a permeate fraction having an increased concentration of normal butane.

Although the lower reflux operation of the distillation will result in less isobutane being provided as the lower boiling fraction (at a given isobutane concentration in the lower boiling fraction), the membrane separation in accordance with this aspect of the invention recovers in the retentate fraction additional amounts of isobutane which can be of suitable purity for commercial purposes or for combination with the lower boiling fraction from the deisobutanizer. In one embodiment of the invention, the retentate may have a higher concentration of isobutane than does the lower boiling fraction and the retentate is used to enrich the combined retentate and lower boiling fraction stream.

A pressure drop is maintained across the membrane in order to effect the desired separation at suitable permeation rates. The membrane may be of any suitable type including diffusion and sieving, and may be constructed of inorganic, organic or composite materials. For diffusion membranes, the driving force is the differential in partial pressures between the retentate and the permeate sides. In sieving membranes, the absolute pressure drop becomes a significant component of the driving force independent of partial pressures or concentrations. The preferred membranes are sieving membranes having a $C_4$ Permeate Flow Index of at least 0.01 and a $C_4$ Permeate Flow Ratio of at least 1.25:1. The sieving membranes are discussed in more detail below.

In the membrane separations, the pressure drop is often in the range of 0.1 to 10, preferably 0.2 to 2, MPa. In practice, the normal butane-containing fraction will be contacted with the retentate side of the membranes without additional compression to minimize capital and operating costs. The temperature for the membrane separation will depend in part on the nature of the membrane and on the temperature of the fraction. Thus, for polymer-containing membranes, temperatures should be sufficiently low that the strength of the membrane is not unduly adversely affected. In most instances, the temperature for the separation is the temperature of the deisobutanizer fraction. Often the temperature is in the range of 25° C. to 150° C. Thus, the conditions of the membrane separation may provide for a liquid or gas or mixed phase on the retentate side of the membrane. The permeate may be a gas, liquid or in a mixed phase. If the fluid on the retentate side of the membrane is in the liquid phase, the permeate may be liquid, gaseous or mixed phase.

The membranes may be in any suitable form such as hollow fibers, sheets, and the like which can be assembled in a separator unit such as bundled hollow fibers or flat plate or spiral wound sheet membranes. The physical design of the membranes should enable, when assembled in the separator unit, sufficient pressure drop across the membrane to provide desirable flux. For hollow fiber membranes, the high pressure side (retentate side) is usually at the outside of the hollow fiber. The flow of the permeate may be co-current, countercurrent or cross-current with respect to the flow of the fluid on the retentate side of the membrane. Sufficient membrane surface area is provided that under steady state conditions the desired isobutane concentration in the retentate fraction is obtained.

At least a portion of the permeate fraction is recycled to the isomerization step.

Sieving Membranes

The preferred sieving membranes may be of various types, for instance, molecular sieves, pore-containing ceramic, metal, polymeric or carbon membranes, or composite membranes having a highly porous polymeric, metallic, molecular sieve, ceramic or carbon support with a thin sieving layer or barrier (molecular sieve), e.g., zeolitic, polymeric, metal, ceramic or carbon, having microporosity.

The membranes may be continuous or discontinuous. A discontinuous membrane comprises an assembly of small particle size microporous barrier whereas a continuous membrane comprises a continuous layer of microporous barrier. The membranes may be formed of a single material or they may be composites containing microporous barrier and support and, optionally, other structure. When making a thin, continuous barrier layer, as the thickness of the sieving layer decreases, the difficulties in obtaining a defect-free layer increase. As the processes of this invention do not require high selectivity, the membranes can contain minor defects. Typically continuous membranes are made by depositing or growing on a meso/macroporous structure, a continuous, thin layer of microporous barrier. Discontinuous assemblies of nano-sized microporous barrier enable very small permeating thicknesses to be achieved, but with the potential of by-pass. Discontinuous membranes use a meso/macroporous structure with which the microporous barrier is associated.

Examples of zeolite barrier include small pore molecular sieves such as SAPO-34, DDR, ALPO-14, ALPO-17, ALPO-18, ALPO-34, SSZ-62, SSZ-13, zeolite 3A, zeolite 4A, zeolite 5A, zeolite KFI, H-ZK-5, LTA, UZM-9, UZM-13, ERS-12, CDS-1, Phillipsite, MCM-65, and MCM-47; medium pore molecular sieves such as silicalite, SAPO-31, MFI, BEA, and MEL; large pore molecular sieves such as FAU, OFF, NaX, NaY, CaY, 13X, and zeolite L; and mesoporous molecular sieves such as MCM-41 and SBA-15. A number of types of molecular sieves are available in colloidal (nano-sized particle) form such as A, X, L, OFF, MFI, and SAPO-34. The zeolites may or may not be metal exchanged.

Other types of sieving materials include carbon sieves; polymers such as PIMs (polymers of intrinsic microporosity) such as disclosed by McKeown, et al., Chem. Commun., 2780 (2002); McKeown, et al., Chem. Eur. J., 11:2610 (2005); Budd, et al., J. Mater. Chem., 13:2721 (2003); Budd, et al., Adv. Mater., 16:456 (2004) and Budd, et al., Chem. Commun., 230 (2004); polymers in which porosity is induced by pore-forming agents such as poly(alkylene oxide), polyvinylpyrrolidone; cyclic organic hosts such as cyclodextrins, calixarenes, crown ethers, and spherands; microporous metal-organic frameworks such as MOF-5 (or IRMOF-1); glass, ceramic and metal shapes into which microporosity has been introduced.

In composite membranes, a meso/macroporous structure is used. The meso/macroporous structure serves one or more functions depending upon the type membrane. It can be the support for the membrane composite, it can be an integral part of forming the microporous barrier, it can be the structure upon which or in which the microporous barrier is located. The meso/macroporous structure can be continuous or discontinuous, and the meso/macroporosity may thus be channels through the material of the meso/macroporous structure or be formed between particles that form the meso/macroporous structure. Examples of the latter are the AccuSep™ inorganic filtration membranes available from the Pall Corp. having a zirconia layer on a porous metal support wherein the zirconia is in the form of spherical crystals.

The meso/macroporous structure preferably defines channels, or pores, in the range of 2 to 500, preferably, 10 to 250, more preferably between 20 and 200, nanometers in diameter, and has a high flux. In more preferred embodiments, the $C_4$ Permeant Flow Index of the meso/macroporous structure is at least 1, and most preferably at least 10, and sometimes at least 1000. The meso/macroporous structure may be isotropic or anisotropic. The meso/macropores may be relatively straight or tortuous.

The meso/macroporous structure may be composed of inorganic, organic or mixed inorganic and organic material. The selection of the material will depend upon the conditions of the separation as well as the type of meso/macroporous structure formed. The material of the meso/macroporous structure may be the same or different than the material for the molecular sieve. Examples of porous structure compositions include metal, alumina such as alpha-alumina, gamma alumina and transition aluminas, molecular sieve, ceramics, glass, polymer, and carbon. In preferred embodiments, defects in the substrate are repaired prior to providing the barrier or precursor to the barrier. In another embodiment, the substrate may be treated with a silica sol to partially occlude pores and facilitate deposition of the barrier or precursor to the barrier. The silica particles will still provide sufficient space between their interstices to allow high flux rates. Another technique is to coat the support with silicon rubber or other polymer that permits high flux but occludes defects in the support or in the barrier.

If the meso/macroporous structure does not so serve, the membrane can contain a porous support for the meso/macroporous structure. The porous support is typically selected on the basis of strength, tolerance for the conditions of the intended separation and porosity.

The AccuSep™ inorganic filtration membranes available from Pall Corp. and similar types of meso/macroporous structures are particularly advantageous since the meso/macroporous structure can be thin thereby avoiding undue thicknesses of molecular sieve being grown. Further, the zirconia is relatively inert to zeolite-forming precursor solutions and synthesis and calcination conditions, making it a preferred meso/macroporous structure for these types of sieving membrane.

High flux is achieved through at least one of the following techniques: first, using a larger pore than required for normal alkane to pass; and second, using an extremely thin pore-containing layer. Where high flux is achieved using larger, less selective micropores in the microporous barrier, adequate separation may be achieved. Often the pores for these types of membranes have an average pore diameter of greater than 5.0 Å (average of length and width), say, 5.0 to 7.0 or 8 Å. Preferably, the structures have an aspect ratio (length to width) of less than 1.25:1, e.g., 1.2:1 to 1:1. For molecular sieve-containing membranes, exemplary structures are USY, ZSM-12, SSZ-35, SSZ-44, VPI-8, and Cancrinite. In some instances, a permeating molecule in a micropore may assist in enhancing selectivity. For instance, a normal hydrocarbon in a pore may decrease the rate at which a branched hydrocarbon can enter the pore as compared to another normal hydrocarbon.

High flux can also be achieved using very thin microporous barrier in either a continuous or discontinuous membrane. The microporous barrier can, if desired, be selected from sieving structures having micropores that are substantially impermeable to the moiety sought to be retained on the retentate side. In general, the pores for these types of membranes have an average pore diameter of up to 5.5 Å, for instance, 4.5 to 5.4 Å. The aspect ratio of the pores of these membranes may vary widely, and is usually in the range of 1.5:1 to 1:1. For molecular sieve-containing membranes, exemplary structures are ZSM-5, silicalite, ALPO-11, ALPO-31, ferrierite, ZSM-11, ZSM-57, ZSM-23, MCM-22, NU-87, UZM-9, and CaA.

Membranes comprising a discontinuous assembly of microporous barrier are characterized in that the barrier has a major dimension less than 100 nanometers, and the microporous barrier is associated with a meso/macroporous structure defining fluid flow pores, wherein barrier is positioned to hinder fluid flow through the pores of the meso/macroporous structure. A molecular sieve barrier is "associated" with a meso/macroporous structure when it is positioned on or in the structure whether or not bonded to the structure. Hence, nano-sized particles or islands of molecular sieve are used as barriers for the membranes. The discontinuous, microporous barrier is positioned to hinder fluid flow through fluid flow channels defined by the meso/macroporous structure. The barrier may be at least partially occluding the opening of a fluid flow channel of the meso/macroporous structure and/or within the fluid flow channel. Due to the small size of the particles or islands forming the discontinuous assembly of microporous barrier, some selectivity of separation is achievable despite the discontinuity.

Typically the size and configuration of the molecular sieve particles and the size and configuration of the meso/macropores in the meso/macroporous structure will be taken into account in selecting the components for the sieving membranes. With more spherical molecular sieve particles, such as silicalite, it is preferred to select a meso/macroporous structure having pores that are close to the same effective diameter. In this manner, the molecular sieve particles, if placed in, or partially in, the pores of the meso/macroporous structure, will provide minimal void space for by-pass. More flexibility exists with platelets and irregular shaped molecular sieve particles as they can overlap with little or no void space. In some instances a combination of molecular sieve configurations may be desirable. For instance, a spherical molecular sieve may be drawn into the pores of a meso/macroporous structure with smaller, more plate-like molecular sieve particles being subsequently introduced. The complementary functions are that the sphere serves as a support for the plate-like particles and the plate-like particles overlap to reduce by-pass. While the molecular sieves will likely be different compositions, and thus have different microporosity size and configuration, the benefit is enhanced separation without undue loss of permeance.

Where zeolitic molecular sieves are used, obtaining small particles is important to obtaining the high flux in a discontinuous microporous barrier. For many zeolites, seed particles are available that are less than 100 nanometers in major dimension. Most molecular sieves are made using organic templates that must be removed to provide access to the cages. Typically this removal is done by calcination. As discussed later, the calcination may be effected when the template-containing molecular sieves are positioned in a macropore such that undue agglomeration is avoided simply by limiting the number of particles that are proximate. Another technique for avoiding agglomeration of the zeolite particles during calcination is to silate the surface of the zeolite, e.g., with an aminoalkyltrialkoxysilane, aminoalkylalkyldialkoxysilane, or aminoalkyldialkylalkoxysilane. The amount of silation required will depend upon the size of the zeolite and its composition as well as the conditions to be used for calcination. In general, between 0.1 to 10 millimoles of silane are used per gram of zeolite.

Various techniques exist for providing the molecular sieve particles on or in the meso/macroporous support in a manner that at least partially occludes the meso- or macropores in the support. The specific technique to be used will depend upon the size and configuration of the molecular sieve particles, the size and configuration of the meso/macropores in the meso/macroporous structure, and the desired placement of the molecular sieve in or on the meso/microporous structure.

Especially where molecular sieve is placed on the surface of a meso/macroporous structure to occlude at least a portion of the opening of the pores, the meso/macroporous structure may be wet with a solution, or suspension, of nano-sized molecular sieve. The concentration of molecular sieve in the suspension should be sufficiently low that upon drying, the resulting layer of molecular sieve is not unduly thick. Advantageously at least a slight pressure drop is maintained across the meso/macroporous structure during the coating such that a driving force will exist to draw molecular sieve to any pores in the meso/macroporous structure that have not been occluded. Usually the suspension will be an aqueous suspension, although suspensions in alcohols and other relatively inert liquids can be used advantageously, at a concentration of between 2 and 30, say 5 and 20, mass percent. Where a pressure differential is used, the pressure differential is generally in the range of 10 to 200 kPa. One or more coats of molecular sieve may be used, preferably with drying between coats. Drying is usually at an elevated temperature, e.g., between 30° C. and 150° C., for 1 to 50 hours. Vacuum may be used to assist drying. Where zeolites are used as the molecular sieve, calcining, e.g., at a temperature of between 450° C. and 600° C. may, in some instances, assist in securing the molecular sieve to the meso/macroporous structure. Calcining may also serve to agglomerate the molecular sieve particles and thus reduce voids and the size of voids. Calcining, of course, is not essential to the broad aspects of this invention and is only required where, for example, template resides in the micropores.

Where the discontinuous assembly of nano-sized molecular sieve is located outside the pores of the meso/macroporous structure, it may be desirable to bond at least a portion of the particles to the surface of the structure. This can be accomplished in a number of ways. For instance, the surface of the structure can be functionalized with hydroxyl groups or other moieties that would be reactive with a zeolitic molecular sieve. For polymeric molecular sieves, the surface may be functionalized with moieties that react, such as addition or condensation, with functional moieties on the polymer. These techniques are well known in the art for other applications.

Similar preparation techniques can be used where it is desired to incorporate at least a portion of the molecular sieve particles in the pores of the meso/macroporous structure. The molecular sieve particles should be of an appropriate size to enter the meso/macropores. A pressure differential may be used to draw barrier particles into the pores or ultrasonication may be used to aid in getting barrier particles into the pores of the meso/macroporous support. The depth of the molecular sieve particles in the pores of the meso/macroporous structure should not be so great as to unduly reduce permeance. Often, any surface deposition of molecular sieve is removed by, e.g., washing.

If desired, zeolitic molecular sieves can be grown in situ in the pores of the meso/macroporous structure to provide a discontinuous membrane. The synthesis may provide discrete particles or islands between other structure such as the meso/macroporous structure or other particles.

An example of using other particles to make discontinuous membranes of zeolitic molecular sieves, involves providing silica, which may have a particle size of between 5 and 20 nanometers, in or on the meso/macroporous structure. The silica, due to the active hydroxyls on the surface, serves as a nucleating site for a zeolite-forming, precursor solution, and layers of zeolite can be grown on and between the silica particles.

Materials other than silica particles can be used as nucleating sites including other molecular sieves or seed crystals of the same zeolite. The surface of the meso/macroporous structure can be functionalized to provide a selective location for zeolite growth. Some zeolites have self nucleating properties and thus may be used in the absence of nucleating sites. Examples of these zeolites are FAU and MFI. In these situations, it may be desired to maintain the precursor solution under zeolite forming conditions for a time sufficient that growth of the zeolite starts prior to contacting the precursor solution with the meso/macroporous structure.

For example, one method to form a barrier layer is to place a zeolitic molecular sieve precursor liquid on a meso/microporous structure. The precursor is permitted to crystallize under hydrothermal crystallization conditions, after which the membrane is washed and heated to remove residual organic material. The molecular sieve material resides primarily in and occludes the pores of the porous substrate.

The molecular sieve may be of any suitable combination of elements to provide the sought pore structure. Aluminum, silicon, boron, gallium, tin, titanium, germanium, phosphorus and oxygen have been used as building blocks for molecular sieves such as silica-alumina molecular sieves, including zeolites; silicalite; AlPO; SAPO; and boro-silicates. The precursor includes the aforementioned elements, usually as oxides or phosphates, together with water and an organic structuring agent which is normally a polar organic compound such as tetrapropyl ammonium hydroxide. Other adjuvants may also be used such as amines, ethers and alcohols. The mass ratio of the polar organic compound to the building block materials is generally in the range of 0.1 to 0.5 and will depend upon the specific building blocks used. In order to prepare thin layers of molecular sieves in the membranes, it is generally preferred that the precursor solution be water rich. For instance, for silica-alumina molecular sieves, the more ratio of water to silica should be at least 20:1 and for aluminophosphate molecular sieves, the mole ratio should be at least 20 moles of water per mole of aluminum.

The crystallization conditions are often in the range of 80° C. to 250° C. at pressures in the range of 100 to 1000, frequently 200 to 500, kPa absolute. The time for the crystallization is limited so as not to form an unduly thick layer of molecular sieve. In general, the crystallization time is less than 50, say, 10 to 40, hours. Preferably the time is sufficient to form crystals but less than that required to form a molecular sieve layer of 200 nanometers, say, 5 to 50 nanometers. The crystallization may be done in an autoclave. In some instances, microwave heating will effect crystallization in a shorter period of time. The membrane is then washed with water and then calcined at 350° to 550° C. to remove any organics.

Especially with some zeolitic molecular sieve materials, making particles less than 100 nanometers is troublesome. Moreover, even with the use of seed crystals, the particle size may be larger than desired. Another embodiment in making a discontinuous barrier membrane is to synthesize the zeolite in open regions between particles (substrate particles) having a major dimension less than 100 nanometers. Accordingly, the major dimension of the microporous barrier can be less than 100 nanometers. The substrate particles serve as a nucleating site for the zeolite formation and thus are selected from materials having capability of nucleating the growth of the zeolite. Examples of such materials are silica, especially silica having a major dimension of between 5 and 50 nanometers and other zeolites having major dimensions less than 100 nanometers. The use of fumed silica as the substrate particle is particularly useful for making an AlPO microporous barrier.

The growth of the zeolite on the substrate particle may occur before or after the substrate particle is used in forming the membrane composite.

Advantageously, the growth of the zeolite on the substrate particles occurs while drawing the synthesis liquor through the composite. This technique helps ensure that the growth occurs not as a layer on top of the particles, but in the interstices between the particles. The pressure drop increases as the zeolite growth occurs, and the pressure drop can be used as an indicator when adequate zeolite formation has occurred.

Polymeric molecular sieves can be synthesized in the meso/macroporous structure. One method for synthesizing a small polymeric molecular sieve is to functionalize nanoparticles and/or the meso/macroporous structure with a group that can react with an oligomer such as through a condensation or addition reaction. For instance, the functional groups may provide a hydroxyl, amino, anhydride, dianhydride, aldehyde, amic acid, carboxyl, amide, nitrile, or olefinic moiety for addition or condensation reaction with a reactive moiety of an oligomer. Suitable oligomers may have molecular weights of 30,000 to 500,000 or more and may be reactive oligomers of polysulfones; poly(styrenes) including styrene-containing copolymers; cellulosic polymers and copolymers; polyamides; polyimides; polyethers; polyurethanes; polyesters; acrylic and methacrylic polymers and copolymers; polysulfides, polyolefins, especially vinyl polymers and copolymers; polyallyls; poly(benzimidazole); polyphosphazines; polyhydrazides; polycarbodiides, and the like.

The synthesis in situ of the molecular sieve, whether it be inorganic or organic, can be under suitable conditions. A preferred technique involves conducting the synthesis while drawing the reactant solution, e.g., the precursor solution or oligomer solution through the meso/macroporous structure. This technique provides the benefit of directing the reactant solution to voids that have not been occluded as well as limits the extent of growth of the molecular sieve as no fresh reactant will be able to enter the reaction site once the molecular sieve has occluded the meso- or macropore.

The molecular sieve on polymer support membranes or polymeric supports themselves may also be pyrolyzed in a vacuum furnace to produce a carbon membrane. For such membranes containing molecular sieves, the pore structure of the carbon support is preferably of sufficient diameter to minimize the resistance to the flow of fluids with the molecular sieve structure doing the separation. The temperature of the pyrolysis will depend upon the nature of the polymer support and will be below a temperature at which the porosity is unduly reduced. Examples of polymeric supports include polyimides, polyacrylonitrile, polycarbonates, polyetherketones, polyethersulfones and polysulfones, and prior to pyrolysis, the supports have pores or openings in the range of 2 to 100, preferably 20 to 50, nanometers.

Continuous membranes may be prepared by any suitable technique. Typically, the thickness of the microporous barrier will be related to the duration of the deposition or growth of the microporous barrier on the meso/macroporous structure. The microporous barrier may be formed by reducing the pore size of an ultrafiltration membrane (effective pore diameters of 1 to 100 nanometers) or a microfiltration membrane (effective pore diameters of 100 to 10,000 nanometers) by, e.g., organic or inorganic coating of the channel either interior of the surface, or preferably, at least partially proximate to the opening of the channel. The deposited material serves to provide a localized reduction of the pores or openings through the support to a size which permits the desired sieving without unduly reducing the diameter of the remaining pore structure in the support. Examples of vapor depositable materials include silanes, paraxylylene, alkylene imines, and alkylene oxides. Another technique for reducing pore size is to deposit a coke layer on the meso/macroporous structure. For instance, a carbonizable gas such as methane, ethane, ethylene or acetylene can be contacted with the structure at sufficiently elevated temperature to cause coking. The preferred porous supports are ultrafiltration membranes having pore sizes of between 1 and 80, preferably between 2 and 50, nanometers.

For zeolitic, continuous membranes, one fabricating technique involves contacting the surface of the meso/macroporous structure with precursor for molecular sieve and growing the molecular sieve for a time sufficient to achieve the sough film thickness. The procedures disclosed above can be used to synthesize the molecular sieve. In some instances, it may be desirable to occlude, e.g., with a wax, the meso/macropores of the support to prevent undue growth of zeolite in those pores. The wax can subsequently be removed.

Various techniques are available to enhance the selectivity of high flux membranes. Numerous techniques exist to cure defects in continuous or discontinuous membranes. As the membranes need not exhibit high $C_4$ Permeate Flow Ratios to be useful for many applications, any technique that increases resistance to flow through the defects will serve to improve membrane performance. For instance, a silica sol overlay coating may be used to occlude interstitial openings between the molecular sieve crystals or remaining large pores in the support regardless of how the membrane is prepared.

Another technique to occlude large pores is to provide on one side of the barrier layer a large, reactive molecule which is not able to permeate the micropores of the barrier and on the other side a cross linking agent. The major defects, and to some extent the minor defects become filled with the large, reactive molecule and are fixed by crosslinking. The unreacted large molecule component can then be removed as well as unreacted crosslinking agent. The large molecule may be an oligomer or large molecule.

For discontinuous membranes, solid may be provided in at least a portion of the voids between particles or islands of microporous barrier and between the microporous barrier and the meso/microporous structure.

One generic technique for enhancing the selectivity of a sieving membrane is to agglomerate adjacent particles of molecular sieve to reduce or substantially eliminate voids between the particles and between the particles and walls of the pore structure in the meso/macroporous structure. Because the particles are nano-sized and the number of adjacent particles can be relatively few, the agglomeration can occur while still retaining desirable Permeant Flow Rates. For polymeric molecular sieves that are thermoplastic, the agglomeration can occur by heating to a temperature where agglomeration occurs but no so high as to lose either its microporous structure or its ability to provide the desired occlusion of the meso- or macropore of the meso/macroporous structure. Agglomeration can also be accomplished by calcining zeolitic molecular sieves. Calcining tends to agglomerate small zeolite particles, especially particles that are neither silated nor otherwise treated to reduce the tendency to agglomerate. The temperature and duration of the calcining will depend upon the nature of the zeolitic molecular sieve. Usually temperatures of between 450° C. and 650° C. are employed over a period of between 2 and 20 hours.

The agglomeration technique may be used with respect to molecular sieve particles that are on the surface of the meso/macroporous structure as well as those within the pores of the structure. Most preferably, agglomeration is used when the molecular sieve particles are located within the meso- or macropores of the meso/macroporous structure such that the major dimension of the agglomerate is less than 200, preferably less than 100, nanometers. The agglomeration may be effected with or without a pressure differential across the membrane. Preferably a pressure differential is used to assist in reducing voids through which fluid can by-pass the molecular sieve.

Another generic technique where the discontinuous assembly of barrier defines voids is to at least partially occlude at least a portion of the voids by a solid material therein. Preferably the solid material is a polymer or inorganic material. The solid material may simply reside in the void or it may adhere or be bonded to the molecular sieve or meso/macroporous structure. The solid material may be a particle or oligomer that may be preformed and then introduced into the voids or it may be formed in situ.

In one aspect, the solid material provides a "mortar" with the microporous barrier particles. The mortar is typically a suitable polymeric material that can withstand the conditions of the separation. Representative polymers include polysulfones; poly(styrenes) including styrene-containing copolymers; cellulosic polymers and copolymers; polyamides; polyimides; polyethers; polyurethanes; polyesters; acrylic and methacrylic polymers and copolymers; polysulfides, polyolefins, especially vinyl polymers and copolymers; polyallyls; poly(benzimidazole); polyphosphazines; polyhydrazides; polycarbodiides, and the like. Preferred polymers are those having porosity such as PIMs (see WO 2005/012397) and polymers in which porosity has been induced by pore forming agents. These polymers have pores that may be 0.3 or more, preferably at least 1, nanometer in major dimension and hence allow for fluid flow to and from the barrier particles.

It is not necessary that all particles be encased in the mortar. Often the average thickness of the mortar layer is less than 100 nanometers, and is preferably no more than the major dimension of the particles. If too much mortar is used, a mixed membrane structure may result, and flux unduly penalized. Hence, the mass ratio of barrier particles to mortar often is in the range of between 1:2 to 100:1, preferably between 3:1 to 30:1.

The mortar and particles may be admixed, e.g., in a slurry, and then placed in association with the microporous structure, or may be provided after deposition of the particles. The polymer may be formed in situ at the region containing the barrier particles. The barrier particle may be inert to the polymerization or may have active sites to anchor a polymer. For instance, the particle may be functionalized with a reactive group that can bind with the polymer or with monomer undergoing polymerization, say, through a condensation or addition mechanism such as discussed above.

A concern is that the mortar occludes the micropores of the molecular sieve. With highly porous polymer such as the PIMs, the effect of any occlusion can be attenuated. Often, the amount of polymer used for the mortar and its molecular weight and configuration is such that insufficient polymer is present for encapsulating all the molecular sieve particles. Frequently, the mass ratio of polymer to molecular sieve is between 0.01:1 and 0.3:1. The weight average molecular weight of the polymer is sometimes in the range of 20,000 to 500,000, preferably, between 30,000 and 300,000.

The mortar may be other than polymeric. For example, where the molecular sieve is a zeolite, a silicon tetraalkoxide can react with the zeolite and can through hydrolysis form a silica framework or mass between the molecular sieve particles. Usually a dilute aqueous solution of silicon tetraalkoxide is used, e.g., containing between 0.5 and 25 mass percent silicon tetraalkoxide, to assure distribution. The functionalization of the zeolite with silicon tetraalkoxide also is useful as a cross-linking site with organic polymer, especially those containing functional groups such as hydroxyl, amino, anhydride, dianhydride, aldehyde or amic acid groups that can form covalent bonds with organosilicon alkoxide. Also, the same or different zeolite may be grown between the zeolite particles and the zeolite particles and the meso/macroporous structure using the techniques described above.

Yet another approach to reducing bypass is to use two or more sized particles in forming the barrier-containing layer. If, for example, the microporous barrier particles are generally spherical with a nominal major dimension of 60 nanometers, the regions between the particles can be sizable and enable bypass. Incorporating configurationally compatible particles in these regions can hinder fluid flow and thus result in a greater portion of the fluid being directed to the barrier particles for the selective separation. The configuration of the barrier particles will depend upon the type of barrier particle used. A microporous zeolitic molecular sieve particle having a major dimension of less than 100 nanometers will likely have a defined configuration due to its crystalline structure. Some zeolites tend to have a platelet-type configuration whereas others, such as AlPO-14, have a rod-like structure. Similarly, polymeric, ceramic, glass and carbon molecular sieve particles may have configurations that are not readily changed. Hence, the configuration of the open regions between particles can vary widely.

Sometimes, the configurationally compatible particles are selected to achieve at least partial occlusion of the region. Thus, for spherical barrier particles rod shaped or much smaller configurationally compatible particles may be desired. The configurationally compatible particles may be of any suitable composition given the size and conditions of operation. The particles may be polymeric, including oligomeric; carbon; and inorganic such as fumed silica, zeolite, alumina, and the like.

With reference to FIG. 1, a butane-containing feedstock is supplied to an isomerization unit via line 102. As shown, the feedstock is introduced into line 122 between deisobutanizer 116 and membrane separator 124. Alternatively, the feedstock can be introduced into the isomerization unit via deisobutanizer 116 as described below. Hydrogen is provided via line 104 and is combined with a normal butane-containing permeate fraction in line 126. The combined stream passes as isomerization feed to isomerization reactor 106. The effluent from isomerization reactor 106 is directed via line 108 to stabilizer column 110. In stabilizer column 110, lights and chloride-containing components are removed as an overhead via line 112. The lights may be used for any suitable purpose including for fuel value. The bottoms from stabilizer column 110 are passed through line 114 to deisobutanizer 116. An overhead is provided via line 118 from deisobutanizer 116. A bottoms stream from deisobutanizer 116 is removed via line 120. A normal butane-containing side stream from deisobutanizer 116 is passed via line 122 to the retentate side of membrane separator 124. A stream enriched in isobutane is removed from separator 124 via line 128 and is combined with overhead in line 118. The permeate fraction is recycled via line 126 to isomerization reactor 106.

Figure 2:
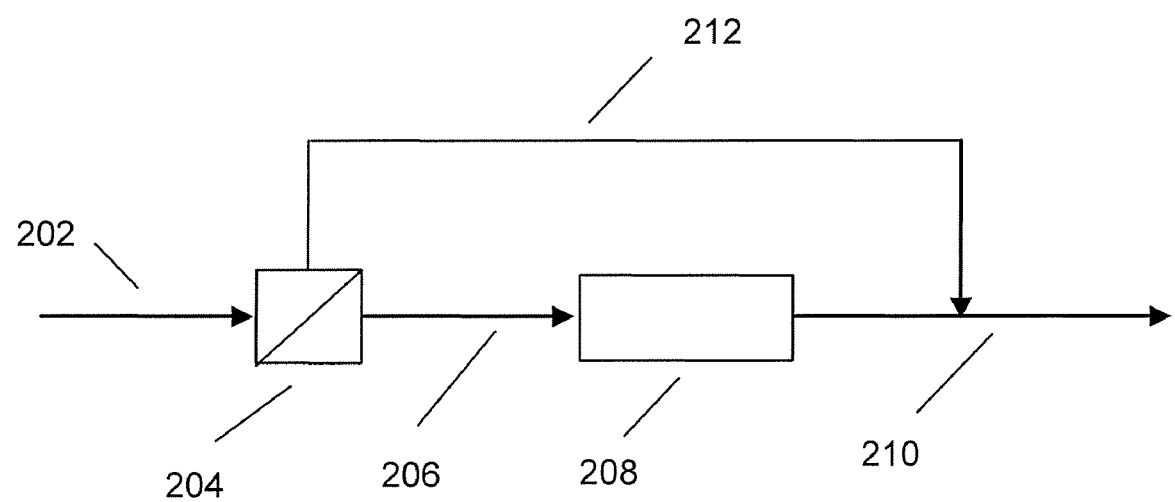
FIG. 2 is a schematic representation of processes in accordance with this invention where a normal butane-containing feedstock is subjected to membrane separation to provide an isobutane-containing effluent that is combined with the isomerization effluent to provide a product without the necessity to distill isobutane from normal butane.

With reference to FIG. 2, normal butane-containing feedstock is supplied by line 202 to the retentate side of membrane separator 204. A permeate containing an increased concentration of normal butane is passed via line 206 to isomerization reactor 208 to provide an isomerization effluent that is withdrawn via line 210. Not shown is a stabilizer to remove chloride components and lights from the isomerization effluent. The retentate from membrane separator 204 is passed via line 212 for combination with the isomerization effluent to provide an isobutane product. By way of example, assuming that the feedstock contains 50 mass-% normal butane and 50 mass-% isobutane and assuming that the retentate stream contains 75 percent of the isobutane in the feedstock at a purity of 95 mass-% and the isomerization provides an equilibrium distribution of 60 mass-% isobutane to 40 mass-% normal butane, the combined product stream has an isobutane concentration of nearly 75 mass-%.

The invention claimed is:

1. An apparatus for the isomerization of feedstock containing normal butane comprising:
    (a) an isomerization reactor (106) adapted to isomerize normal butane to an isobutane-containing isomerate having an inlet and an outlet for isomerate;
    (b) a distillation column (116) having an inlet in fluid communication with the outlet of isomerization reactor (106) a lower boiling fraction outlet conduit (118) and a higher boiling fraction outlet conduit (122), said distillation column (116) being adapted to distill at least a portion of the isobutane-containing isomerate to provide a lower boiling fraction richer in isobutane than the isomerate and a higher boiling fraction richer in normal butane than the isomerate, said higher boiling fraction containing isobutane; and
    (c) a membrane separator (124) having a feed side inlet in fluid communication with the higher boiling fraction conduit (122), a feed side outlet in fluid communication with line (118) from the lower boiling outlet of distillation column (116), and a permeate outlet in fluid communication with the inlet of the isomerization reactor (106).

2. The apparatus of claim 1 wherein permeate outlet is also in fluid communication with the isomerization reactor.

3. The apparatus of claim 1 wherein the membrane is a sieving membrane having a $C_4$ Permeate Flow Index of at least 0.01 and a $C_4$ Permeate Flow Ratio of at least 1.25:1.

4. The apparatus of claim 3 wherein the sieving membrane has an average pore diameter of 5.0 to 7.0 Å.

5. The apparatus of claim 3 wherein the sieving membrane has an average pore diameter of 4.5 to 5.4 Å.

* * * * *